United States Patent [19]

Takaku et al.

[11] Patent Number: 4,552,955
[45] Date of Patent: Nov. 12, 1985

[54] PROCESS FOR THE SYNTHESIS OF 4′,5′-UNSATURATED NUCLEOSIDES

[75] Inventors: Hiroshi Takaku, Chiba; Takeshi Noda, Kanagawa; both of Japan

[73] Assignee: Sankyo Chemical Company, Limited, Tokyo, Japan

[21] Appl. No.: 393,254

[22] Filed: Jun. 29, 1982

[30] Foreign Application Priority Data

Jun. 29, 1981 [JP] Japan ................................. 56-99708
Jun. 29, 1981 [JP] Japan ................................. 56-0699709

[51] Int. Cl.$^4$ .......................................... C07H 17/00
[52] U.S. Cl. .......................................... 536/24; 536/23
[58] Field of Search .................................... 536/23, 24

[56] References Cited

U.S. PATENT DOCUMENTS

| | | | |
|---|---|---|---|
| 3,472,837 | 10/1969 | Verheyden et al. | 536/23 |
| 3,585,189 | 6/1971 | Verheyden et al. | 536/23 |
| 3,928,319 | 12/1975 | Jenkins et al. | 536/27 |
| 3,998,806 | 12/1976 | Townsend | 536/24 |
| 4,038,033 | 7/1977 | Monks et al. | 536/29 |

FOREIGN PATENT DOCUMENTS 0004797 1/1983 Japan ................................. 536/24

OTHER PUBLICATIONS

C. T. Thurber et al., *J. Org. Chem.*, vol. 41, p. 1041 (1976).
H. Bauer, *Chem. Ber.*, vol. 46, p. 92 (1913).
*J.C.S. Perkin I*, pp. 1786 to 1791 (1977).
*J. Org. Chem.*, vol. 40, No. 20, pp. 2920 to 2923 (1973).
*J. Med. Chem.*, vol. 22, No. 6, pp. 653 to 657 (1979).
*J. Med. Chem.*, vol. 41, No. 10, p. 1841 (1976).
*J. Carbohydrates-Nucleosides-Nucleotides*, 5 (4), p. 369 (1978).
*J. Med. Chem.*, 24, pp. 515 to 520 (1981).
*Chem.-Biol. Interactions*, 22, p. 219 (1978).
*Bulletin of the Chemical Society of Japan*, vol. 50 (10), pp. 2689 to 2693 (1977).
*J. Chem. Soc.*, p. 1368 (1928).

Primary Examiner—Ethel G. Love
Attorney, Agent, or Firm—Sughrue, Mion, Zinn, Macpeak, and Seas

[57] ABSTRACT

Process for the production of 4′,5′-unsaturated nucleosides via a novel compound, 5′-Se-(2- or 4-nitrophenyl)-selenonucleoside, is disclosed, said selenonucleoside being represented by the formula

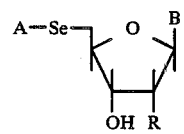

wherein R is a hydrogen atom or a hydroxyl group, A is 2- or 4-nitrophenyl group and B is a base.

18 Claims, No Drawings

PROCESS FOR THE SYNTHESIS OF 4',5'-UNSATURATED NUCLEOSIDES

FIELD OF THE INVENTION

The present invention relates to a process for the synthesis of 4',5'-unsaturated nucleosides and, more particularly, to a process for the synthesis of 4',5'-unsaturated nucleosides using a novel compound 5'-Se-(2- or 4-nitrophenyl)selenonucleoside as a starting material.

BACKGROUND OF THE INVENTION

Compounds 4',5'-unsaturated nucleosides represented by the formula (I):

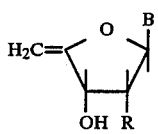

wherein R represents a hydrogen atom or a hydroxyl group and B represents a base group such as a purine base and pyrimidine base, for example, 4',5'-unsaturated adenosine, are important intermediates for the synthesis of nucleocidine [E. J. Backus, H. D. Tresner and T. H. Campbell, *Antibiot. Chemother.*, Vol. 7 p. 532 (1957)] and augustmycin A. [H. Yüntsen, K. Ohkuma, Y. Ishii and H. Yonehara; *J. Antibiot.*, ser. A. 9 P. 195 (1956)]; nucleocidine and angustmycin A are known to possess potent trypanocidal, antibacterial, and antimicrobial activities.

These compounds and methods of preparation are already known [I. D. Jenkins, J. P. H. Verheyden and J. G. Moffatt, *J. Amer. Chem. Soc.*, Vol. 93 P. 4323 (1971); E. J. Prisbe, J. Smejkal, J. P. H. Verheyden and J. G. Moffatt, *J. Org. Chem.*, Vol. 41 P. 1836 (1976)]. 4',5'-Unsaturated nucleosides have hitherto been synthesized by, for example, the reaction as shown below.

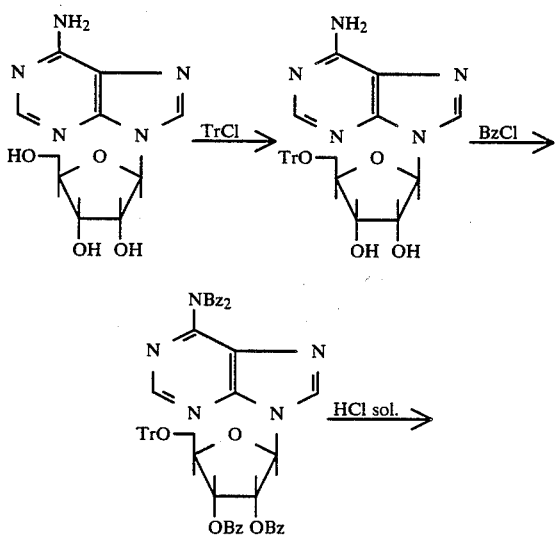

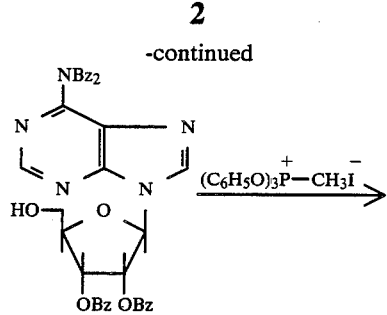

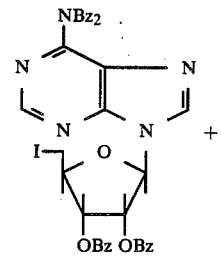

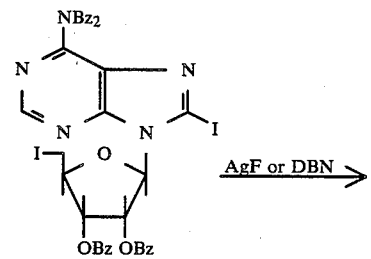

(by-product)

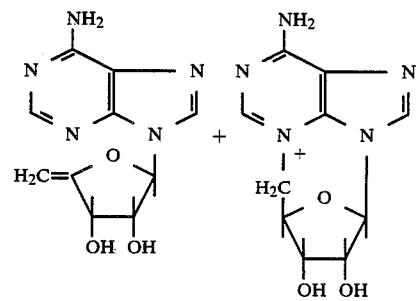

(by-product)

Bz: benzoyl
Tr: Triphenylmethyl
DBN: 1,5-diazabicyclo[4,3,0]non-5-ene

As is seen in the reaction formula, however, the protection of the base and sugar moieties of nucleoside is required so that the process becomes complicated. Furthermore, undesired side reactions such as halogenation of the base moiety and cyclization take place, resulting in low yield of 4',5'-unsaturated nucleoside. Accordingly, there has been a demand for a solution to these problems.

SUMMARY OF THE INVENTION

Therefore, an object of the present invention is first to remedy the foregoing drawbacks and provide a process for synthesizing 4',5'-unsaturated nucleosides readily and in high yield.

Another object is to provide a useful starting material for the synthesis of the foregoing 4',5'-unsaturated nucleosides.

Still another object is to provide a process for the synthesis of a useful starting material.

Having made assiduous investigations of processes for the synthesis of 4′,5′-unsaturated nucleosides, the inventors have found that novel 5′-Se-(2- or 4-nitrophenyl)selenonucleosides represented by the formula (II):

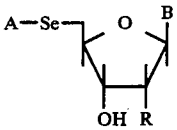

wherein R represents a hydrogen atom or a hydroxyl group, A represents 2- or 4-nitrophenyl group and B represents a base, are a useful starting material for the synthesis of 4′,5′-unsaturated nucleosides, which can readily be synthesized in high yield by reacting selenoxide derivatives resulting from the reaction between the 5′-Se-(2- or 4-nitrophenyl)selenonucleosides and hydrogen peroxide, with a tertiary amine. Thus the present inventors have completed the present invention based on these findings.

DETAILED DESCRIPTION OF THE INVENTION

According to the present invention, 4′,5′-unsaturated nucleosides can be easily synthesized in high yield in the course of reaction represented by the following equation:

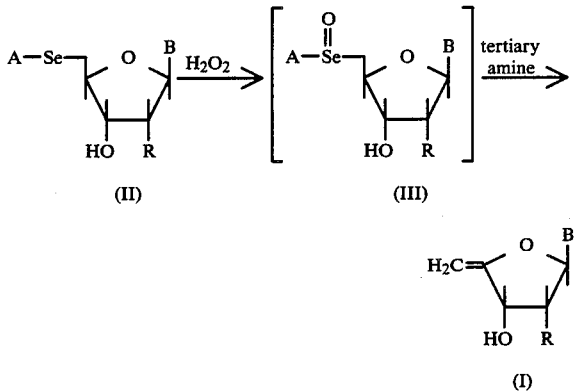

wherein R, A and B each represents the same as defined above.

In the present invention, a 30% hydrogen peroxide solution is added to a 5′-Se-(2- or 4-nitrophenyl)-selenonucleoside (II) preferably in an amount of 5 to 15 molar equivalents, more preferably 10 molar equivalents, in the presence of an aprotic inert solvent such as tetrahydrofuran and dioxane, and the reaction is carried out at room temperature (10°–30° C.) for 1–3 hours with stirring, whereupon a selenoxide (III) is produced quantitatively. After the reaction is complete, the solvent is evaporated and the residue dissolved in a solvent such as pyridine, dimethylsulfoxide, dimethylformamide, etc. To the resulting solution is added a tertiary amine such as triethylamine, pyridine and collidine preferably in an amount of 1 to 12 equivalents, more preferably 10 equivalents, and the reaction is carried out at room temperature to 100° C., preferably 50° C., for 6–12 hours to eliminate the

moiety, whereby a 4′,5′-unsaturated nucleoside (I) is obtained. It is surprised that the elimination reaction does not accompany a side chain such as cyclization, in contrast to a conventional method. Therefore, high yield can be achieved. In this reaction, as a solvent, pyridine and dimethylsulfoxide each gives the best results; as a tertiary amine, triethylamine and pyridine are particularly preferred; and the reaction temperature is preferably higher than a room temperature so as to obtain the quantitative yield. After the reaction is complete, the solvent is evaporated completely and the residue treated with, for example, an ion-exchange resin to give a pure 4′,5′-unsaturated nucleoside (I).

In the synthesis of 4′,5′-unsaturated nucleoside described above, 5′-Se-(2-nitrophenyl)selenonucleoside is preferably used because it gives higher yield than 5′-Se-(4-nitrophenyl)selenonucleoside.

The 5′-Se-(2- or 4-nitrophenyl)selenonucleoside represented by the general formula (II), an excellent starting material for the synthesis of the foregoing 4′,5′-unsaturated nucleoside, is a new compound and obtained by reacting a 2- or 4-nitrophenylselenocyanide (IV) with n-butylphosphine and a nucleoside (V) as shown in the following reaction formula:

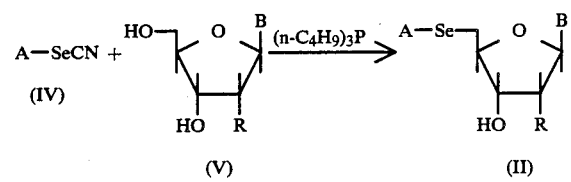

wherein R, A and B each represents the same as defined above.

The desired product (II) can be obtained in an almost quantitative yield by reacting the nucleoside (V) with 2- or 4-nitrophenylselenocyanide ($O_2$NPhSeCN) (IV) preferably in an amount of 1 to 5 equivalents, more preferably 3 equivalents, and n-butylphosphine (n-$Bu_3$P) preferably in an amount of 2 to 10 equivalents, preferably 6 equivalents, in pyridine. The reaction is carried out at a room temperature for 30 minutes to 24 hours. In this reaction, reduced amounts of $O_2$NPhSeCN and n-$Bu_3$P lower the yield of the product and the reaction using ($O_2$NPhSe)$_2$ or (PhSe)$_2$ in place of $O_2$NPhSeCN will not give the desired product (II). The desired product (II) can be obtained as a pure compound by evaporating the pyridine after the completion of the reaction followed by treating the residue by silica gel column chromatography. The nucleoside (V) which is used in the above reaction is commercially available or can be produced by a conventional method, as described in, for example, C. T. Thurber et al, *J. Org. Chem.*, vol. 41 p. 1041 (1976). The 2- or 4-nitrophenylselenocyanide (IV) can be easily produced by the method described in H. Bauer, *Chem. Ber.*, vol. 46 p. 92 (1913).

In the synthesis of 5′-Se-(2- or 4-(nitrophenyl)-selenonucleocide (II), the cyano group of 2- or 4-nitrophenylselenocyanide (IV) selectively reacts with the 5′-hydroxy group of the nucleoside (V). This reaction provides advantages that proceeds quantitatively, and the protection of the base and sugar moieties of nucleoside which is required is a conventional method can be omitted. Further, the base of nucleoside can be freely selected since the base part is out of the reaction site.

Examples of the base represented by B in the foregoing formulae are listed in the table below.

TABLE

| Base | Stucture | Substituents |
|---|---|---|
| purinyl group which may be substituted at the 2-, 6- and/or 8-positions | (purine ring, positions 1-9) | 2-, 6-positions: a hydrogen atom, an amino group which may be substituted by an alkyl group or an acyl group, or a keto group 8-position: a hydrogen atom, or a halogen atom. |
| pyrimidinyl group which may be substituted at the 2-, 5- and/or 6-positions | (pyrimidine ring, positions 1-6) | 2-, 6-positions: a hydrogen atom, an amino group which may be substituted by an alkyl group or an acyl group, or a keto group 5-position: a hydrogen atom, an alkyl group, a halogen atom, or a cyano group |
| pyrazolyl group which may be substituted at the 3- and/or 4-positions | (pyrazole ring, positions 1-5) | 3-, 4-positions: a hydrogen atom, an amino group which may be substituted by an alkyl group or acyl group, a hydroxy group, a halogen atom, a carbamoyl group, a mercapto group, a keto group, or a cyano group |
| imidazolyl group which may be substituted at the 4- and/or 5-positions | (imidazole ring, positions 1-5) | 4-, 5-positions: a hydrogen atom, an amino group which may be substituted by an alkyl group or an acyl group, a hydroxy group, a halogen atom, a carbamoyl group, a mercapto group, a keto group, or a cyano group |
| triazolyl group which may be substituted at the 3-position | (triazole ring, positions 1-5) | 3-position: a hydrogen atom, an amino group which may be substituted by an alkyl group, a hydroxy group, a halogen atom, a carbamoyl group, a mercapto group, a keto group, or a cyano group |
| tetrazolyl group | (tetrazole ring) | |
| succinimido group wherein the nitrogen atom may be substituted | (succinimide ring) | a hydrogen atom, an alkyl group, or an acyl group. |
| etenocytosine | (etenocytosine ring) | |

TABLE-continued

| Base | Stucture | Substituents |
|------|----------|--------------|
| etenoadenine | (structure) | |

Note: The alkyl group as herein used has 1 to 3 carbon atoms.

It is worth special mention that, whereas in the foregoing known synthetic methods the protection of the base and sugar moieties of nucleoside is indispensable, in the present invention, as will be easily understood from the foregoing two reaction formulae in the synthesis of 4′,5′-unsaturated nucleoside (I) and 5′-Se-(2- or 4-nitrophenyl)selenonucleoside (II), the protection is unnecessary. Accordingly the base and the sugar can be chosen without any limitation and the desired compound can be obtained in good yield under mild conditions.

The 4′,5′-unsaturated nucleoside of the present invention is a compound which is utilizable for the synthesis of a variety of antibiotics and agricultural chemicals, etc. Therefore, the new synthetic process disclosed herein is a very useful synthetic method.

The present invention will now be explained in more detail by reference to the following examples, but the present invention is not limited thereto.

EXAMPLE 1

Adenosine (524 mg, 2 mM) and 2-nitrophenylselenocyanide (1.13 g, 6 mM) were added to pyridine (7 ml). To the resulting mixture was added under cooling n-butylphosphine (2.42 ml, 12 mM) and then the mixture was stirred at room temperature for 24 hours. After the reaction was complete, water (1 ml) was added to the reaction mixture and the resulting mixture was allowed to stand at room temperature for 30 minutes and concentrated under reduced pressure. The residue was treated by silica gel chromatography to provide 884 mg (yield: 98%) of 5′-Se-(2-nitrophenyl)selenoadenosine, mp. 127°–129° C.

UV: $\lambda_{max}^{MeOH}$ 256 nm.

NMR (DMSO-d$_6$): δ 3.66 (m, 2H, C′$_5$-H), 4.20 (m, 1H, C′$_4$-H), 4.40 (m, 1H, C′$_3$-H), 4.89 (t, 1H, $J_{1',2'}$=6Hz, $J_{2',3'}$=6Hz, C′$_2$-H), 5.52 (d, 1H, $J_{2',3'}$=6Hz, 3′-OH) 5.69 (d, 1H, $J_{1',2'}$=6Hz, C$_1$′-H), 7.31 (br-s, 2H, NH$_2$) 7.42-8.38 (m, 6H, Ar, C$_2$-H, C$_8$-H).

Elementary analysis: (C$_{16}$H$_{16}$H$_6$O$_5$Se, H$_2$O): C: 40.55 (40.94), H: 3.63 (3.86), N: 17.76 (17.79).

Figures outside the parentheses show found values and those inside the parentheses calculated ones. The same applied to the following examples.

EXAMPLE 2

Into pyridine (30 ml) were dissolved thymidine (727 mg, 3 mM) and 2-nitrophenylselenocyanide (1.02 g, 4.5 mM). To the solution was added under cooling n-butylphosphine (1.22 ml, 5 mM). The temperature of the resulting mixture was restored to room temperature and the mixture was, after stirring for 1 hour, concentrated under reduced pressure. The residue was dissolved in methylene chloride and the solution washed with water. The methylene chloride was evaporated and the residue treated by silica gel column chromatography to yield 1.15 mg (yield: 90%) of 5′-Se-(2-nitrophenyl)-selenothymidine.

mp. 166°–168° C.

UV: $\lambda_{max}^{MeOH}$ 256 nm, 272(Sh)nm.

Elementary analysis: (C$_{16}$H$_{17}$N$_6$O$_6$Se): C: 45.16 (45.07), H: 4.06 (4.03), N: 9.84 (9.86).

EXAMPLE 3

Into pyridine (22 ml) were dissolved uridine (542 mg, 2.22 mM) and 2-nitrophenylselenocyanide (756 mg, 3.33 mM). To the resulting solution was added under cooling n-butylphosphine (0.902 ml, 3.7 mM). The mixture, whose temperature was restored to room temperature, was stirred for 30 minutes. The reaction mixture was concentrated under reduced pressure and the residue treated by silica gel column chromatography to give 834 mg (yield: 89%) of 5′-Se-(2-nitrophenyl)selenouridine.

mp. 132°–134° C.

UV: $\lambda_{max}^{MeOH}$ 254 nm.

Elementary analysis: (C$_{15}$H$_{15}$N$_3$O$_7$Se): C: 42.01 (42.06), H: 3.61 (3.54), N: 9.73 (9.81).

EXAMPLE 4

5′-Se-(2-nitrophenyl)selenoadenosine (902 mg, 2 mM) was added to tetrahydrofuran (50 ml). To the mixture was added under cooling a 30% hydrogen peroxide solution (20 mM), and the resulting mixture, whose temperature was restored to room temperature, was stirred for 2 hours. After the reaction was complete, the solvent was evaporated completely. The residue was dissolved into pyridine (10 ml) and thereto was added triethylamine (2.8 ml, 20 mM). After the resulting mixture had been reacted at 50° C. for 12 hours, the pyridine was evaporated and the residue treated with an ion-exchange resin to give 483 mg (yield: 97%) of pure 4′,5′-unsaturated adenosine, 9-(5′-deoxy-β-D-eliso-pento-4-enofuranosyl)adenine.

mp. 184°–185° C.

UV: $\lambda_{max}^{MeOH}$ 259 nm (ε=14300).

Elementary analysis: (C$_{10}$H$_{11}$N$_5$O$_3$): C: 48.41 (48.19), H: 4.43 (4.45), N: 28.03 (28.10).

EXAMPLE 5

5′-Se-(2-nitrophenyl)selenothymidine (852 mg, 2 mM) was added to tetrahydrofuran (50 ml). To the mixture was added under cooling a 30% hydrogen peroxide solution (20 ml). The mixture, whose temperature was restored to room temperature, was stirred for 2 hours. After the reaction was complete, the solvent was removed completely and the residue dissolved into pyridine (10 ml). Thereto was added triethylamine (2.8 ml, 20 mM) and the reaction was carried out at 50° C. for 6 hours. The reaction mixture was worked up in the same manner as in Example 4 to afford 380 mg (yield:

85%) of the corresponding 1-(2',5'-deoxy-β-D-glyceropento-4-enofuranosyl)thymine.

mp. 196°–198° C.

UV: $\lambda_{max}^{MeOH}$ 267 nm ($\epsilon$=9500).

Elementary analysis: ($C_{10}H_{12}N_2O_4$): C: 53.98 (53.57), H: 5.58 (5.40), N: 12.65 (12.50).

EXAMPLE 6

Except for the use of 5'-Se-(2-nitrophenyl)selenouridin (856 mg, 2 mM), the reaction and the post-treatment were carried out in the same manner as in Example 5 to afford 442 mg (yield: 90%) of 1-(5'-deoxy-β-D-erythropento-4-enofuranosyl)uracil.

mp. 169°–170° C.

UV $\lambda_{max}^{MeOH}$ 261 nm ($\epsilon$=9600).

Elementary analysis: ($C_9H_{10}N_2O_5$): C: 47.89 (47.79), H: 4.62 (4.46), N: 12.21 (12.39).

While the invention has been described in detail and with reference to specific embodiments thereof, it will be apparent to one skilled in the art that various changes and modifications can be made therein without departing from the spirit and scope thereof.

What is claimed is:

1. A process for the production of a 4',5'-unsaturated nucleoside represented by the formula (I):

[Structure (I): $H_2C=$ furanose ring with O, B, OH, R substituents]

wherein R is a hydrogen atom or a hydroxyl group and B is a base selected from the group consisting of a purinyl group, a pyrimidinyl group, a pyrazolyl group, an imidazolyl group, a triazolyl group, a tetrazolyl group, a succinimido group, entenocytosine and entenoadenine; provided that B is a purinyl group, a pyrimidinyl group or a triazolyl group when R is a hydrogen atom, which process comprises:

(1) reacting a 5'-Se-(nitrophenyl)selenonucleoside represented by the formula (II):

[Structure (II): A—Se—CH2— furanose ring with O, B, OH, R substituents]

wherein R and B each has the same meaning as defined above and A is 2- or 4-nitrophenyl group, with hydrogen peroxide to obtain a selenoxide derivative, and (2) reacting said selenoxide derivative with a tertiary amine.

2. A process as claimed in claim 1, which further comprises reacting a nitrophenylselenocyanide represented by A-SeCN wherein A is 2- or 4-nitrophenyl group, n-butylphosphine and a nucleoside represented by the formula (V):

[Structure (V): HO—CH2— furanose ring with O, B, OH, R substituents]

wherein R is said hydrogen atom or a hydroxyl group and B is a base, prior to said reaction (1).

3. A process as claimed in claim 1 or 2, wherein said A is 2-nitrophenyl group.

4. A process as claimed in claim 1, wherein said base is a purinyl group represented by the formula:

[Purine ring structure with positions 1N, 2, 3N, 4, 5, 6, 7N, 8, 9N]

wherein at least one of the 2-, 6- or 8-position is substituted, at the 2- or 6-positions with a hydrogen atom, an amino group which may be substituted by an alkyl group or an acyl group, or a keto group, and at the 8-position with a hydrogen atom or a halogen atom or a pyrimidinyl group represented by the formula:

[Pyrimidine ring structure with positions 1N, 2, 3N, 4, 5, 6]

wherein at least one of the 2-, 5- or 6-position is substituted, at the 2- or 6-positions with a hydrogen atom, an amino group which may be substituted by an alkyl group or an acyl group, or a keto group, and at the 5-position with a hydrogen atom, an alkyl group, a halogen atom or a cyano group.

5. A process as claimed in claim 4, wherein said base is adenine, thymine or uracil.

6. A process as claimed in claim 4, wherein said A is the 2-nitrophenyl group.

7. A process as claimed in claim 1 or 2, wherein said tertiary amine is selected from the group consisting of triethylamine, pyridine, and collidine.

8. A process as claimed in claim 7, wherein said tertiary amine is triethylamine or pyridine.

9. The process of claim 1 wherein said hydrogen peroxide is present in an amount of 5 to 15 molar equivalents.

10. A process as claimed in claim 9 which is carried out in the presence of an aprotic inert solvent.

11. A process as claimed in claim 1, wherein step (1) is carried out at 10° to 30° C. for 1-3 hours with stirring.

12. A process as claimed in claim 1, wherein said tertiary amine is added in an amount of 1 to 12 equivalents.

13. A process as claimed in claim 1, wherein step (2) is carried out at room temperature to 50° C. for 6–12 hours.

14. A process as claimed in claim 2, wherein said nitrophenyl selenocyanide is used in an amount of 1 to 5 equivalents.

15. A process as claimed in claim 2, wherein n-butylphosphine is present.

16. A process as claimed in claim 15, wherein the amount of n-butylphosphine is 2 to 10 equivalents.

17. Process as defined in claim 1, wherein B is a base selected from the group consisting of a purinyl group, a pyrimidinyl group, a pyrazolyl group, an imidazolyl group, a triazolyl group, a tetrazolyl group and a succinimido group.

18. A selenoxide derivative represented by the formula (III):

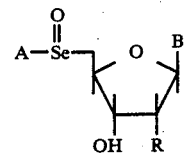

wherein R is a hydrogen atom or a hydroxyl group, A is 2- or 4-nitro-phenyl group and B is a base selected from the group consisting of a purinyl group, a pyrimidinyl group, a pyrazolyl group, an imidazolyl group, a triazolyl group, a tetrazolyl group, a succinimido group, entenocytosine and entenoadenine, provided that B is a purinyl group, a pyrimidinyl group or a triazolyl group when R is a hydrogen atom.

* * * * *